(12) United States Patent
He (10) Patent No.: US 10,295,484 B2
(45) Date of Patent: May 21, 2019

(54) METHOD AND APPARATUS FOR EXTENDING ANGULAR COVERAGE FOR A SCANNING TWO-DIMENSIONAL X-RAY DETECTOR

(71) Applicant: Bruker AXS, Inc., Madison, WI (US)

(72) Inventor: Bob Baoping He, Hercules, CA (US)

(*) Notice: Subject to any disclaimer, the term of this patent is extended or adjusted under 35 U.S.C. 154(b) by 275 days.

(21) Appl. No.: 15/479,335

(22) Filed: Apr. 5, 2017

(65) Prior Publication Data
US 2018/0292334 A1    Oct. 11, 2018

(51) Int. Cl.
*G01N 23/207* (2018.01)
(52) U.S. Cl.
CPC ..... *G01N 23/207* (2013.01); *G01N 2223/056* (2013.01); *G01N 2223/1016* (2013.01); *G01N 2223/33* (2013.01); *G01N 2223/62* (2013.01)
(58) Field of Classification Search
CPC ............. G01N 23/20; G01N 23/20058; G01N 23/207; G01N 2223/33; G21K 1/06

USPC ...................................................... 378/70, 71
See application file for complete search history.

(56) References Cited

U.S. PATENT DOCUMENTS 9,897,559 B2 *  2/2018  He .................. G01N 23/20016

\* cited by examiner

*Primary Examiner* — Jurie Yun
(74) *Attorney, Agent, or Firm* — Benoit & Côté Inc.

(57) ABSTRACT

A method and apparatus for performing an X-ray diffraction measurement with a diffractometer having an X-ray beam directed at a sample and a two-dimensional X-ray detector includes the performance of a physical scan during which the detector is moved through a scanning range in an angular direction about the sample position. To provide a uniform exposure time, the detector, when located at an extreme of the scanning range, is controlled to progressively change the portion of the detected X-ray energy that is used at a rate that maintains a uniform exposure time for each angular position in the scanning range. Alternatively, when located at an extreme of the range, the detector is kept stationary until a desired minimum exposure time is obtained for each angular position, after which the collected diffraction data is normalized relative to exposure time.

32 Claims, 9 Drawing Sheets

METHOD AND APPARATUS FOR EXTENDING ANGULAR COVERAGE FOR A SCANNING TWO-DIMENSIONAL X-RAY DETECTOR

BACKGROUND OF THE INVENTION

Field of the Invention

This invention relates generally to the field of X-ray diffraction and, more specifically, to scanning two-dimensional X-ray diffractometers.

Description of the Related Art

In the field of X-ray diffraction, radiation with a wavelength, A, in the subnanometer range is directed to a crystalline material with a given interatomic spacing, d. When the angle of incidence, θ, relative to the crystalline structure satisfies the Bragg equation, $A=2d \sin θ$, an interferometrically reinforced signal (the diffracted signal), may be observed leaving the material, with an angle of emission being equal to an angle of incidence, both angles being measured with respect to a direction normal to the interatomic spacing of interest.

Figure 1A:
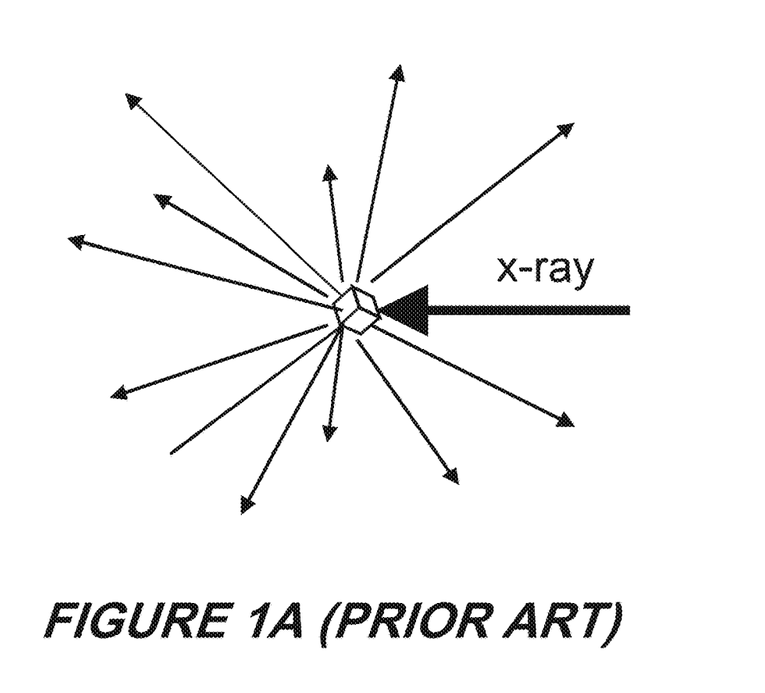
FIG. 1A is a schematic representation of X-rays diffracted from a single crystal sample.
Figure 1B:
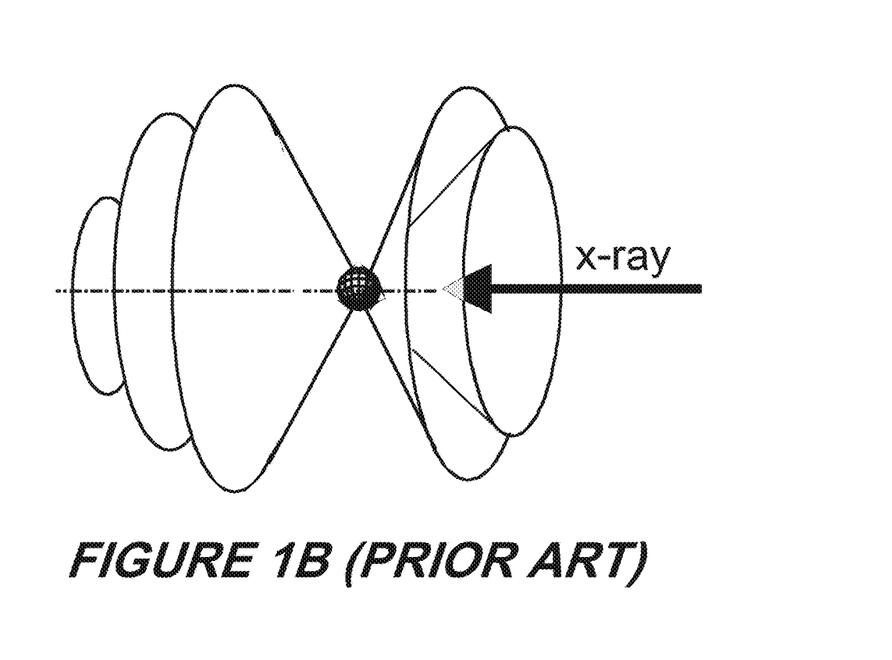
FIG. 1B is a schematic representation of X-rays diffracted from a polycrystalline sample.
Figure 2:
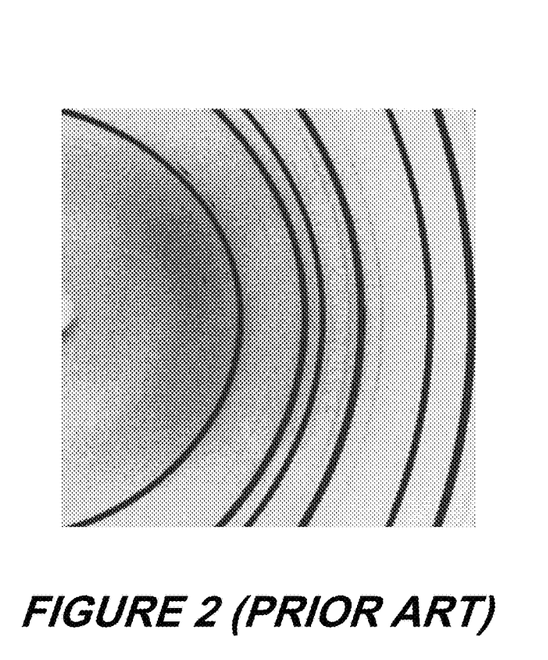
FIG. 2 is an image of a two-dimensional diffraction pattern of corundum showing the corresponding diffraction rings.

Diffracted X-rays from a single crystal sample follow discrete directions each corresponding to a family of diffraction planes, as shown schematically in FIG. 1A. The diffraction pattern from a polycrystalline (powder) sample forms a series diffraction cones, as shown in FIG. 1B, if large numbers of crystals oriented randomly in the space are covered by the incident x-ray beam. Each diffraction cone corresponds to the diffraction from the same family of crystalline planes in all the participating grains. Polycrystalline materials can be single-phase or multi-phase in bulk solid, thin film or fluid. For example, FIG. 2 shows the diffraction pattern of corundum powder collected by a two-dimensional (2D) X-ray detector.

Figure 3:
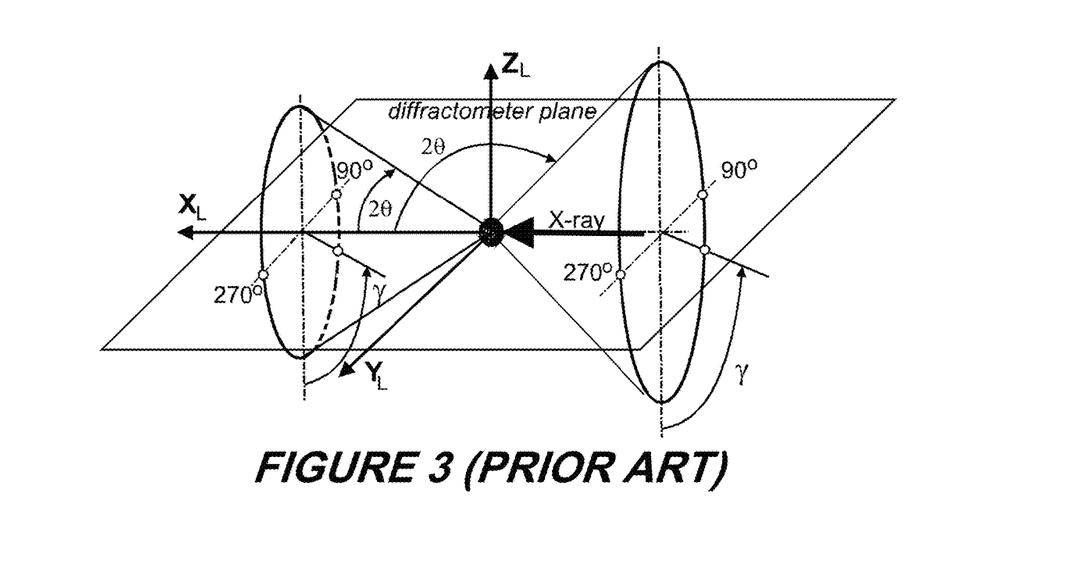
FIG. 3 is a schematic representation of the geometric relationship of diffraction rings in a diffractometer.

FIG. 3 is a schematic illustration showing the geometry of an X-ray diffraction system in the laboratory coordinates system $X_L Y_L Z_L$. The origin of the coordinate system is the instrument center, or goniometer center. The source X-ray beam propagates along the $X_L$ axis, which is also the rotation axis of the diffraction cones. The apex angles of the diffraction cones are determined by the 2θ values given by the Bragg equation. In particular, the apex angles are twice the 2θ values for forward reflection (2θ≤90°) and twice the values of 180°−2θ for backward reflection (2θ>90°). The $X_L$-$Y_L$ plane is the diffractometer plane. The γ angle defines the direction of a diffracted beam relative to the diffraction cone. It is measured within a plane parallel to the $Y_L$-$Z_L$ plane from the point at which the cone intersects the −z portion of the y=0 axis to the point at which the diffracted beam intersects the plane. Thus, a point in the −$Y_L$ portion of the diffractometer plane corresponds to γ=90°, while a point in the +$Y_L$ portion of the diffractometer plane corresponds to γ=270°. Thus, the γ and 2θ angles form a kind of spherical coordinate system which covers all the directions from the origin, where the sample is located.

SUMMARY OF THE INVENTION

In accordance with the present invention, a method and apparatus are provided for performing an X-ray diffraction measurement with an X-ray diffractometer having an X-ray beam directed at a sample. The invention includes a two-dimensional X-ray detector that detects X-ray energy diffracted by the sample, and a scanning system that controls how the detector moves and stores a representation of the detected X-ray energy as a spatial intensity distribution relative to a detection area comprising a cylindrical segment.

In an exemplary embodiment, the detector is moved in an angular direction along a scanning path about a location of the sample while detecting the diffracted X-ray energy. At an extreme of the scanning range, however, the position of the detector is maintained while the portion of the X-ray energy being detected by the detector is changed. In particular, the system progressively changes, along said angular direction, the portion of the X-ray energy being detected that is used to contribute to the stored representation of the detected X-ray energy. This allows for a uniform exposure time to be maintained across an entire scanning range.

In one version of the foregoing embodiment, the extreme of the scanning path is at the beginning of the scanning path, and progressively changing the portion of the X-ray energy being detected that is used to contribute to said representation involves progressively increasing that portion before moving the detector along the scanning path. In another version, the extreme of the scanning path is at the end of the scanning path, and progressively changing the portion of the X-ray energy being detected that is used to contribute to said representation involves progressively decreasing that portion after moving the detector along the scanning path. In still another version of this embodiment, the progressive changing of the portion of the detected X-ray energy used to contribute to the representation occurs at both extremes of the scanning range, in the manner described above for each extreme.

The movement of the detector along the scanning path may be either stepwise or continuous. In either case, the exposure time for the detector is substantially the same for each angular position along the scanning range. The detector may be moved through the angular range at a predetermined speed, and in one version of the invention, the progressive change in the portion of the X-ray energy being detected that is used to contribute to said representation comprises changing that portion at a rate that matches the predetermined speed.

In one variation of the invention, a spatial distribution of the X-ray energy detected by the detector is transformed with a cylindrical projection prior to being used to contribute to the representation of the detected X-ray energy. Thus, the progressive changing of the portion of the X-ray energy being detected that is used to contribute to the stored representation of the detected X-ray energy may occur after the detected X-ray energy is transformed with the cylindrical projection.

In an exemplary embodiment, the detector has a two-dimensional array of pixels. In one version of this embodiment, changing the portion of the X-ray energy being detected that is used to contribute to the stored representation of the detected X-ray energy involves changing the pixels from which detected X-ray energy is used. Pixel columns in the detector may be perpendicular to the scanning path, and changing the pixels from which detected X-ray energy is used may include changing the pixels column-by-column in a direction perpendicular to the pixel columns. In another variation, a spatial distribution of X-ray intensities in the plane of the detector may be stored as a spatial distribution of X-ray intensities in a cylindrical projection of the detector pixels that substantially corresponds to the detection area. In such an arrangement, changing the portion of the X-ray energy being detected that is used to contribute to the stored representation of the detected X-ray energy may include changing the pixels, as projected in the cylindrical projection, from which X-ray intensities are used column-by-column along a direction of the scanning path.

In an alternative embodiment of the invention, the physical scan is performed in a manner similar to that described above, that is, by moving the detector through a scanning range in an angular direction about a location of the sample at a speed of $\Delta\alpha/\Delta t$, where $\Delta\alpha$ is an angular distance that corresponds to the distance between adjacent columns of detector pixels perpendicular to the scan direction, given the distance of the detector from the sample. However, when the detector is located at an extreme of the scanning range, the position of the detector is maintained while actively collecting the diffracted X-ray energy from the whole detector for a duration of $N(\Delta t)$, where N is the number of pixel columns. The measured intensity of the diffracted X-ray energy collected by the detector is then normalized relative to exposure time.

The foregoing embodiment provides a diffraction data set that has a normalized exposure time that is homogeneous throughout the scanning range. The extreme of the scanning range at which the detector is active for the $N(\Delta t)$ duration may be at the beginning of the scanning range, the end of the scanning range, or both. During the movement of the detector, the exposure time is substantially the same for each angular position along the scanning range, and the motion of the detector may be either stepwise or continuous.

DETAILED DESCRIPTION

Figure 4:
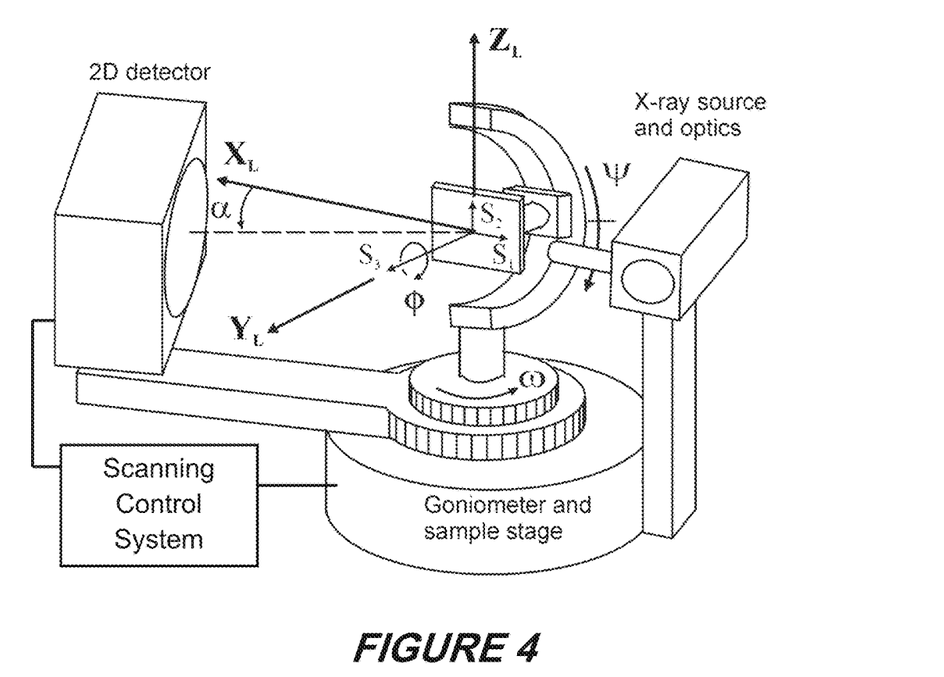
FIG. 4 is a schematic illustration of an X-ray diffractometer with a two-dimensional detector in a horizontal configuration.

FIG. 4 shows the configuration of a horizontal diffractometer with left-hand goniometer and the θ-2θ configuration that may be used with the present invention. As observed by the operator, the goniometer is mounted in the left side of the x-ray tube and primary optics, so the system is categorized as a left-hand system. The diffractometer plane determined by the primary x-ray beam ($X_L$ axis) and the rotation plane of ω and α is in the horizontal position, so the diffractometer is also referred to as a horizontal diffractometer. In this diffractometer, the primary x-ray beam ($X_L$ axis) is fixed. The ω angle is achieved by sample rotation and the α angle is achieved by detector rotation independently. Following the naming scheme of the Bragg-Brentano geometry, this is referred to as a θ-2θ configuration. Also shown schematically in the figure is a scanning control system that controls the movement and activation of the detector. Although shown as a discrete component, those skilled in the art will recognize that the scanning control system may be part of a more integrated control system for the diffractometer.

Figure 5:
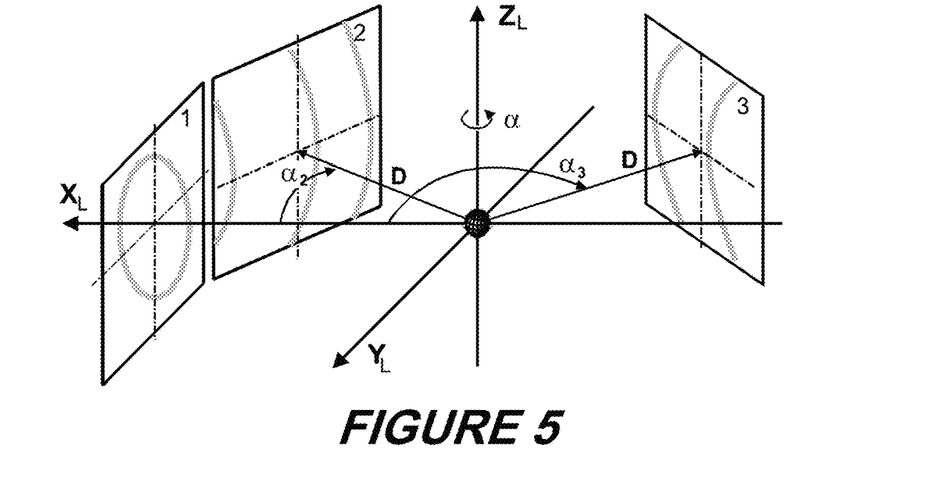
FIG. 5 is a schematic illustration showing diffraction rings detected by a two-dimensional detector at different detector positions in accordance with the present invention.

FIG. 5 is a schematic view of several possible positions of a flat, 2D detector during an X-ray diffraction scan of a powder sample. In this example, the system is shown using laboratory coordinates $X_L Y_L Z_L$. The detection surface can be viewed as a plane which, at each position, intersects the diffraction cone to form a conic section. The detector position is defined by the sample-to-detector distance D and the detector swing angle α. D is the perpendicular distance from the goniometer center to the detection plane and α is a right-handed rotation angle about the $Z_L$ axis. At position 1, the center of the detector is located on the positive side of $X_L$ axis, such that α=0. Each of detector positions 2 and 3 are rotated away from $X_L$ axis with negative swing angles (i.e., α<0), identified, respectively, as $\alpha_2$ and $\alpha_3$. Because of the two-dimensional area of the detector, at a given detector angle α, a range of 2θ values can be measured.

As can be seen from FIG. 5, a diffraction frame collected by a 2D detector at a particular position includes a limited angular range. One way to extend the angular range is by merging multiple frames collected at different swing angles. Another method is to scan over a large 2θ range by rotating the 2D detector about the $Z_L$ axis. As shown schematically in FIG. 6, a 2D detector may be mounted in an orientation that is perpendicular to the diffractometer plane and perpendicular to a line in the diffractometer plane that defines the minimum distance to the detector surface. The length of this line also represents the distance D between the detection plane and the instrument center and, together with the swing angle α, can be used to define the detector position, as described above. The detector swing angle α is defined as the angle measured between the $X_L$ axis and the line between the instrument center and the detection surface.

Figure 6:
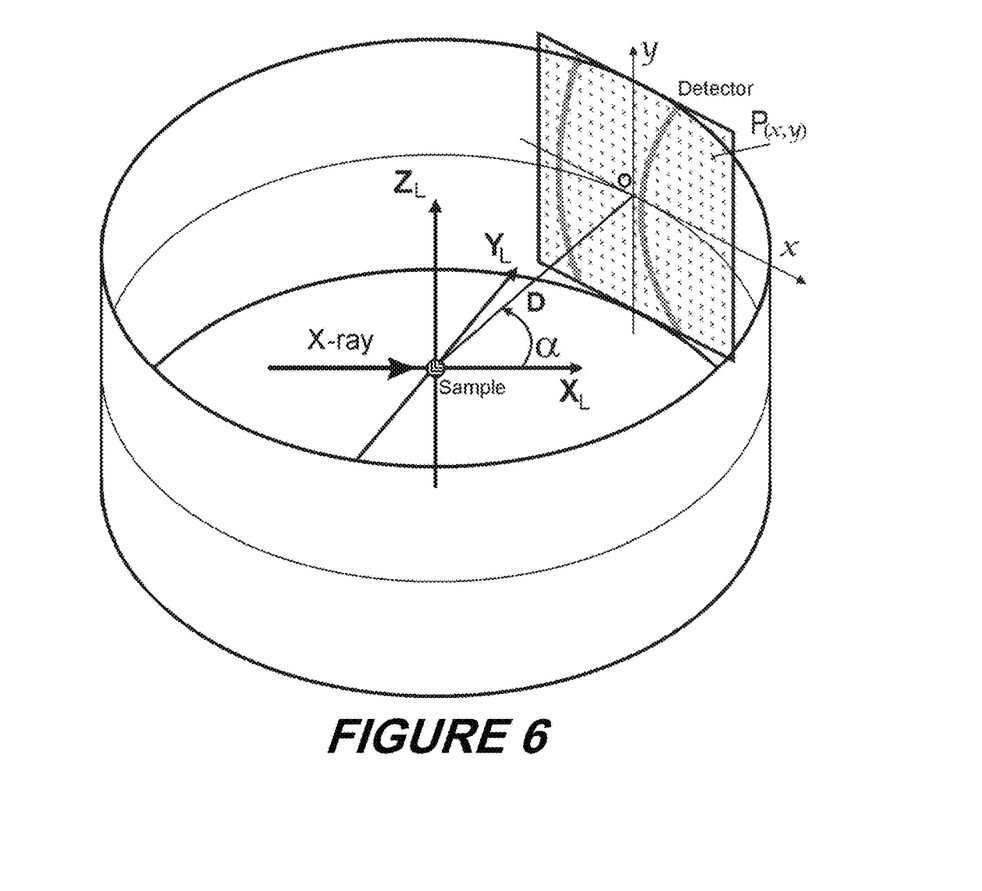
FIG. 6 is a schematic illustration of a two-dimensional detector according to the present invention relative to a detection circle around a sample.

The intersection (o) of the line and detector may be referred to as the detector center, and represents the origin of a two-dimensional x-y coordinate system within the plane of the detector. Thus, the location of any pixel in the 2D detector may be defined by its pixel position (x, y) within this coordinate system. During the data collection scan, the swing angle α changes continuously or in steps while collecting the X-ray counts with the detector. Therefore, during the scan of the detector about the $Z_L$ axis, the y-axis of the detector traces a cylindrical surface during the data collection, as shown in FIG. 6. The X-ray energy detected in the scan is eventually stored as a spatial intensity distribution relative to the detection area, which is typically a segment of the cylindrical surface.

Figure 7A:
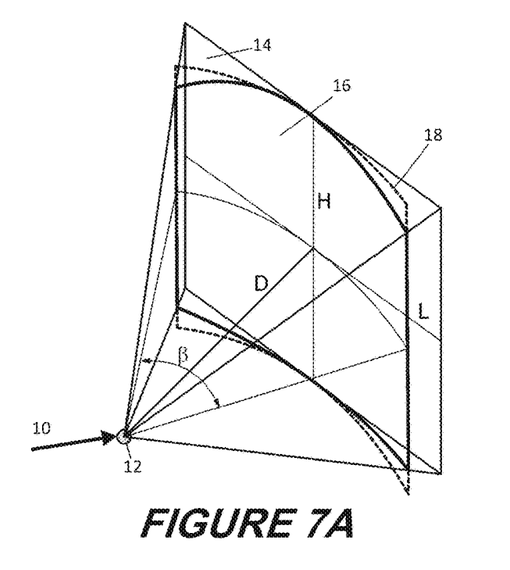
FIG. 7A is a schematic illustration of the projection of a flat two-dimensional X-ray detector to a cylindrical surface.

In order to accurately combine the frames collected at each detector position, the frames are projected to a cylindrical surface based on the respective scattering angle from the incident beam. FIG. 7A depicts a perspective view of a projection showing an initial X-ray beam 10 directed toward a sample 12. A diffraction image 16 is projected toward cylindrical surface 18, indicated in the figure in broken lines. However, as 2D detectors are typically planar, the image projected toward the cylindrical surface is instead collected by flat 2D detector 14, which covers a square (or rectangular) area. The cylindrical surface 18 covers the same angular range (β) in a horizontal direction as the flat detector 14 (relative to the orientation of the figure), and also has the same height (H). However, due to the angles of the diffracted X-rays, the area covered by the flat detector 14 is different from that of the cylindrical surface 18.

Figure 7B:
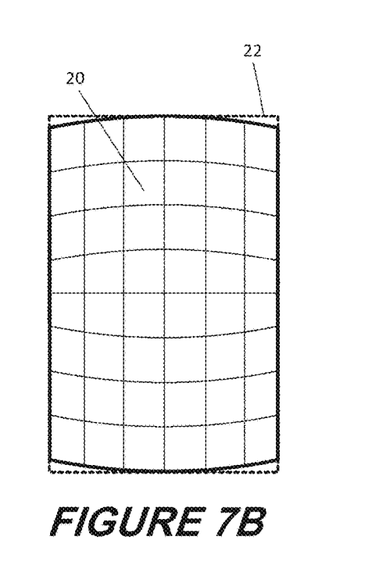
FIG. 7B is a schematic illustration of a projected image on a flattened cylindrical surface, showing the distribution of detector pixels.

FIG. 7B illustrates a flattened cylindrical surface 22 (defined by the broken lines) and a projected image 20. Projected pixels of the diffraction pattern, shown as a grid on the projected image 20, are distorted in shape (e.g., are no long square or rectangular), and the shape and size of each pixel varies according to the original position of the pixel in the flat detector. Details regarding the geometry of the projection are not reproduced herein, but may be found in co-pending U.S. patent application Ser. No. 14/979,305, the relevant portions of which are incorporated herein by reference. The angular coverage of the 2D detector in the horizontal (2θ) direction is given as:

$$\beta = 2\arctan\frac{L}{2D} \quad (2)$$

The accuracy and precision of and evaluation of X-ray diffraction data are significantly affected by counting statistics. Assuming that incident X-rays have a constant flux, the total number of incident X-ray photons at a specified time, t, should be a constant $N_0$. Because X-ray emission and detection are randomly occurring events, the counts measured by a detector or detector pixel in the same time period on the same X-ray beam will not be exactly the same. The statistics of the process can be explained by a Poisson distribution function:

$$P(N) = \frac{N_0}{N!}\exp(-N_0) \quad (3)$$

where N is the total number of X-ray counts measured at the given time t. If the measurement is repeated a large number of times and the values of N are averaged, the average value of N approaches the true value $N_0$, as the number of repeated measurements approaches infinity. For a high number of counts, the Poisson distribution can be expressed approximately as a Gaussian (normal) distribution so that the standard deviation of the measured counts is given as:

$$\sigma = \sqrt{N} = \sqrt{Rt} \quad (4)$$

where R is the count rate. The probability that the true value No is between N±σ is 68.3%, between N±2σ is 95.4%, and between N±3σ is 99.7%. A more revealing expression of the measurement precision can be obtained by multiplying the relative standard deviation, σ/N, by 100% to give the percent standard deviation as:

$$\sigma\% = 100\frac{\sqrt{N}}{N}\% = \frac{100}{\sqrt{N}}\% = \frac{100}{\sqrt{Rt}}\% \quad (5)$$

The percent standard deviation improves as the number of counts increases. At N=1, σ%=100%; at N=100, σ%=10%; at N=10,000, σ%=1%; and at N=1,000,000, σ%=0.1%. It is thus apparent that a larger number of counts or a larger count rate results in a better precision based on the above equations.

During a scanning operation, the swing angle of the 2D detector is changed either continuously or in a step-wise manner, and the image collected by the 2D detector at sequential detector positions is stored as an image of the flattened cylindrical surface. Thus, the stored image is a spatial intensity distribution that represents the 2D diffraction pattern as if the image had been collected by a cylindrical detector of the same 2θ range.

Figure 8:
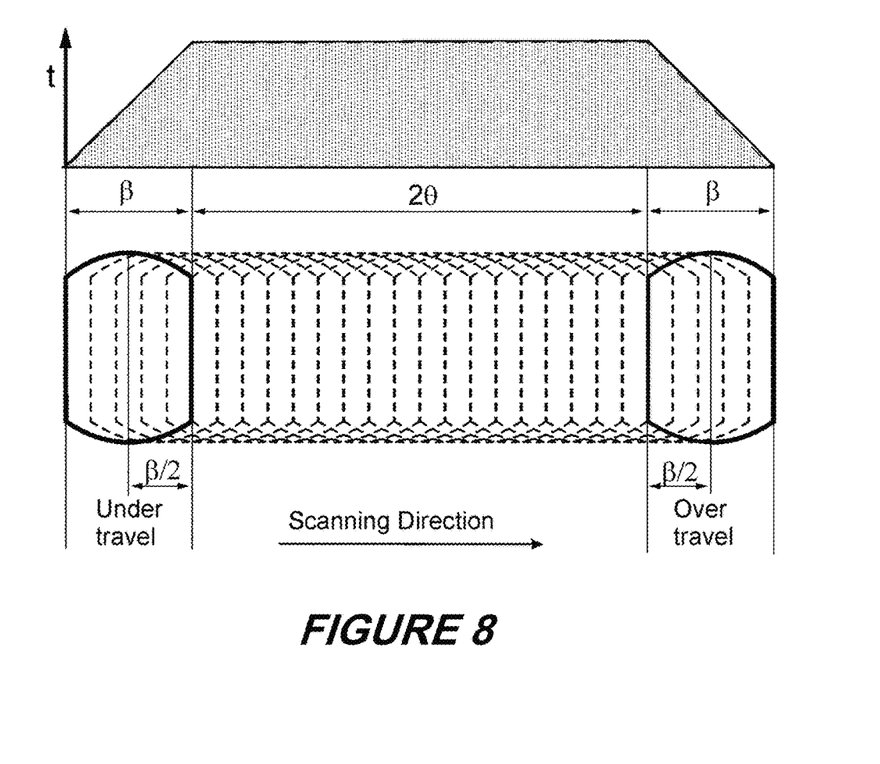
FIG. 8 is a schematic illustration of the use of under travel and over travel scanning to acquire a homogeneous exposure time within a desired 2θ scanning range.

FIG. 8 depicts a linear representation of a series of images taken at sequential positions along the scanning range. As shown, the shape of each image corresponds to the flattened cylindrical surface. In the upper part of FIG. 8 is shown the effective exposure time for each image position along the scanning range of the instrument. Within the center of the 2θ range, the exposure time at each position is the same. However, at the extremes of the range, the overall exposure time is reduced due to the fact that diffracted X-rays at those extremes impinge upon the detector for only a limited number of scanning positions. In order to collect a 2D diffraction pattern with consistent counting statistics, it is necessary to collect the diffraction pattern with homogenous exposure time over the desired 2θ range. The conventional practice is therefore to start the scanning with an "under travel" equivalent to the angular coverage of the 2D detector (β), and finish the scanning with an "over travel" of the same range. Because the swing angle (α) of the 2D detector is based on the center of the detector, the actual start swing angle (α1) has an offset of β/2 before the initial 2θ position, and the finish swing angle (α2) has an offset of β/2 after the final 2θ position, as shown in FIG. 8.

The use of under travel and over travel to collect a 2D diffraction pattern with homogenous exposure time requires adequate space in the diffractometer system for the 2D detector to go beyond the 2θ scanning range. However, this additional space may not always be available or practicable in a given diffractometer. For example, there may be obstacles such as other mechanical components (e.g., the X-ray source, optics, sample monitoring and alignment system or sample stage), or the space necessary for the under travel and over travel may simply not be available given the dimensions of the detector. As discussed hereinafter, however, a method is provided to collect a homogenous diffraction pattern without the need for under/over travel.

Figure 9:
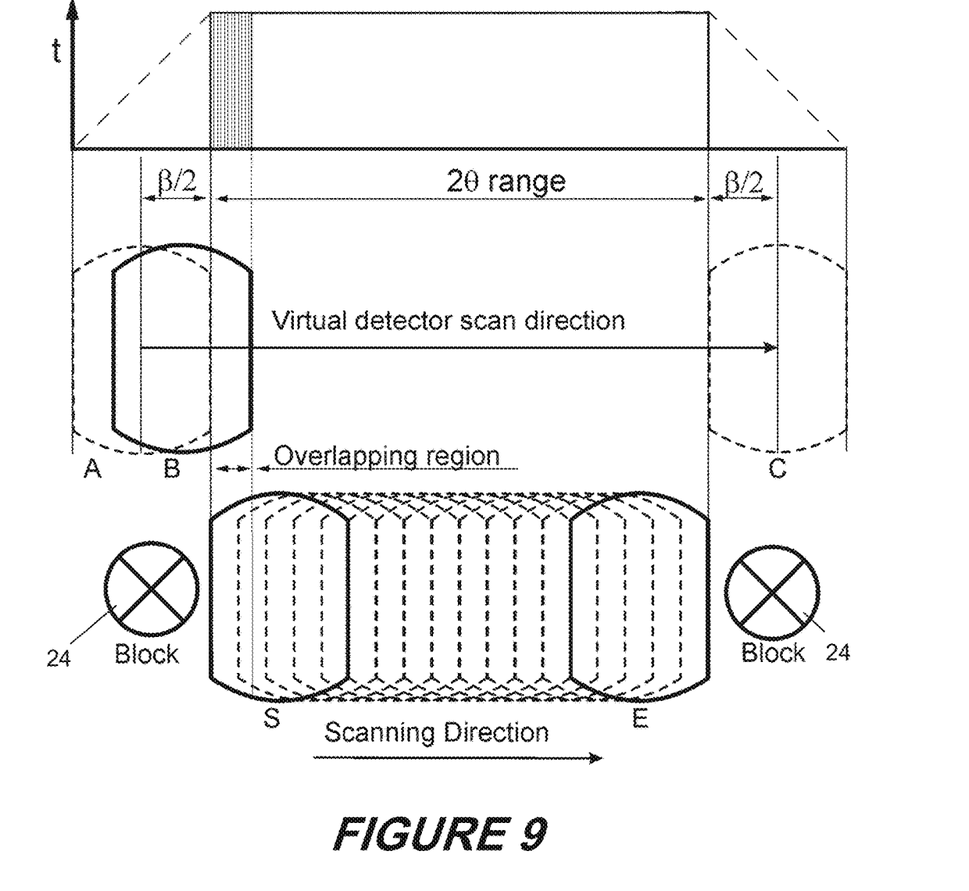
FIG. 9 is a schematic illustration of an embodiment of the invention using a virtual detector method to obtain a homogeneous exposure time.

In the system illustrated in FIG. 9, the desired 2θ range is displayed in the top of the figure. The bottom is the space available for the detector scan between two "blocks" 24, which represent physical obstacles to the 2D detector. Thus, in this example, the physical detector can only scan between detector positions S and E shown in the figure. However, in accordance with the invention, a "virtual detector" is used that can scan between the positions A and C, thereby enabling a homogenous exposure time within the entire 2θ range without requiring the physical detector to extend into the under travel and over travel regions.

The virtual detector is simulated by maintaining the physical detector at an extreme of the scanning path while the portion of the X-ray energy incident on the detector surface is progressively increased or decreased. This allows for additional scanning of an overlapping region by using only the portion of the physical detector that extends into that region. As the virtual detector "moves," the overlapping region changes accordingly, such that only X-ray counts from the appropriate regions are stored in the cylindrical image. In this way, requisite exposure time may be achieved for the entire 2θ range, despite the presence of blocks 24.

Figure 10:
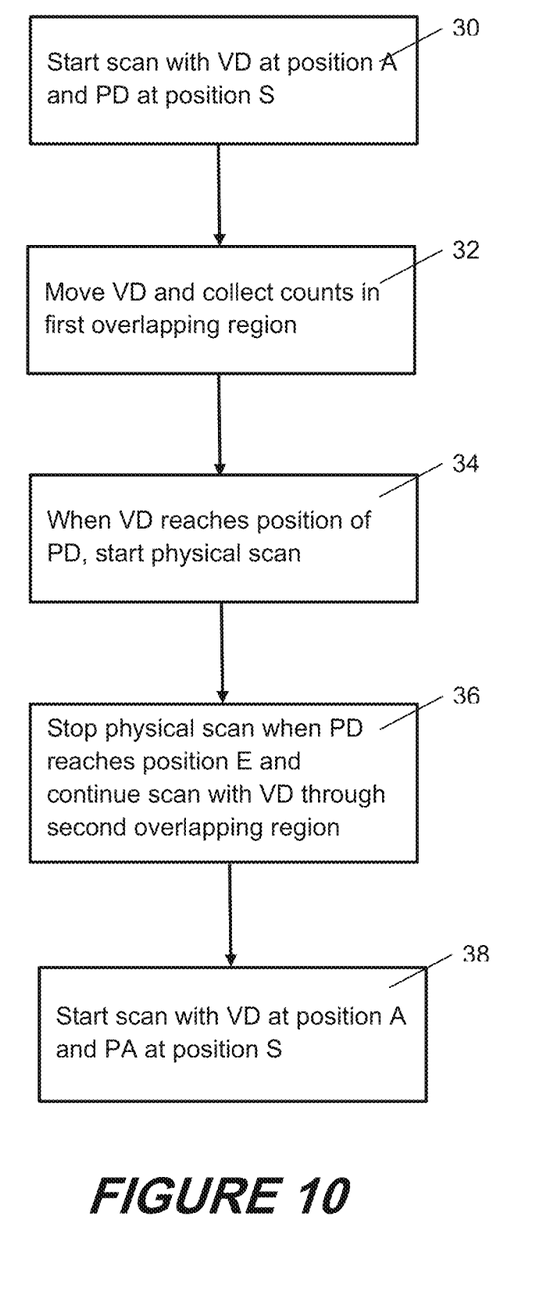
FIG. 10 is a flow diagram showing the method used in the embodiment of FIG. 9.

Making reference to the illustration of FIG. 9, the steps of a scanning method according to the invention are shown in the flow diagram of FIG. 10. The scan is started with the physical detector (PD) located at position S of FIG. 9 (step 30). At this point, the virtual detector (VD) is located at position A, and there is thus no overlap between the position of the physical and virtual detectors. The virtual detector is then "moved" from left to right relative to the orientation of FIG. 9, using the same speed or steps as if the physical detector had been located in the under travel region (step 32).

With the first step of the virtual detector, there is an overlap between the physical detector and the virtual detector equal to the width of the step. At this point, X-ray counts are collected by the physical detector, but only for the overlapping region between the physical and virtual detectors. That is, while the entire surface of the physical detector may be illuminated by diffracted X-rays, only the X-rays detected by those detector pixels residing in the overlapping region are stored in the cylindrical image of the detector. The virtual detector is then advanced to the next position, and the diffracted X-rays detected by the pixels of the overlapping region (which is now larger due to the increased overlap between the physical and virtual detectors) are stored in the cylindrical image. This process continues until the virtual detector reaches the position of the physical detector, at which point there is a total overlap of the two detectors.

The physical scan then begins, with the physical detector being advanced at the same scanning rate, and the diffracted X-rays detected across the entire surface of the detector being stored in the cylindrical image (step 34). The physical scan continues until the physical detector reaches position E shown in FIG. 9. At this point the physical detector is stopped, and the scan is continued with the virtual detector through the second overlapping region (step 36). During this movement of the virtual detector, only the diffracted X-rays detected by the pixels of the physical detector which fall within the overlapping region are stored in the cylindrical image. As the second overlapping region gets progressively narrower as the virtual detector continues through the extended space, the portion of the X-ray energy incident upon the detector surface that is used in forming the cylindrical image therefore decreases accordingly. Once the virtual detector reaches position C shown in FIG. 9, the scan is terminated and data collection by the physical detector is completely stopped (step 38).

Figure 11:
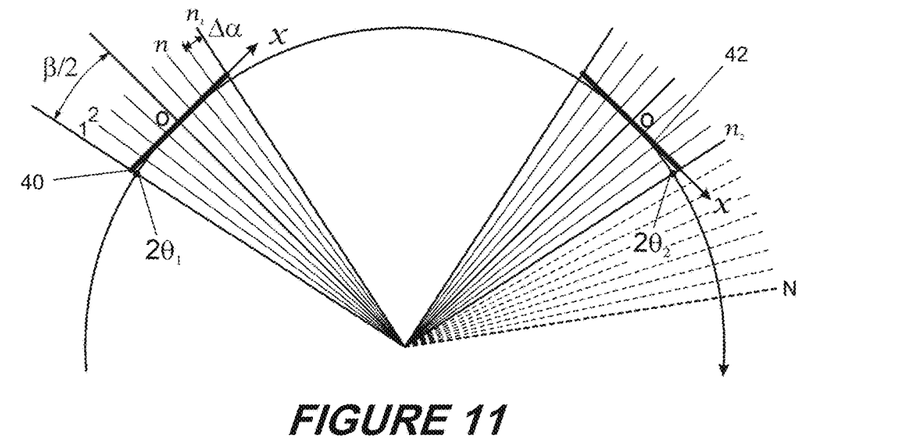
FIG. 11 is a schematic illustration of data collection in the embodiment of FIG. 9 showing virtual and real scanning steps.

Although the foregoing description relies on a discussion of a virtual detector, those skilled in the art will understand that this is only for the purposes of explanation, and that the actual data collection is performed by the physical detector, using proper timing of the detector data collection/storage. FIG. 11 provides an illustration of the data collection using real and virtual scanning steps. The figure provides a schematic view from above, that is, along an axis perpendicular to the goniometer plane. The physical detector is shown at the two extreme positions of its scanning range, at 40 (corresponding to position S of FIG. 9) and at 42 (corresponding to position E of FIG. 9). Each of the radial lines emanating from the goniometer center represents a step along the movement range of the detector. Thus, during the scan, the physical detector starts at position 40, advancing through each step until it arrives at position 42. The virtual detector steps covering the first overlapping region occur while the physical detector is at position 40, while the virtual detector steps covering the second overlapping region occur while the physical detector is at position 42. The virtual detector steps for the second overlapping region are shown in FIG. 11 as broken radial lines.

In FIG. 11, x is the horizontal coordinate axis of the 2D detector, and corresponds to the axis x as illustrated in FIG. 6. The perpendicular axis y is perpendicular to the plane of the figure, and the center of the detector o is also shown. The location of any point/pixel on the 2D detector is therefore given by x and y coordinates, as discussed above. The desired 2θ measurement range is between $2\theta_1$ and $2\theta_2$, and the detector (as measured from the detector center) starts the scan at swing angle $2\theta_1+0.5\beta$, and finishes at swing angle $2\theta_2-0.5\beta$. β is the angular coverage given above by equation (2), and Δα is the angular size of scanning steps. In practice, the image collected with a continuous detector scan should be sampled at fine steps for projection calculation. Unless the continuous scan is done at a relatively low speed and the image projection at a very high speed, a smearing effect will be observed. Therefore, the stepwise scan is preferred unless the smearing effect is negligible.

The steps of the scan are numbered as 1, 2, . . . , n, . . . N, in which n is an arbitrary step and N is the number of the last step. N also represents the total number of the steps, including virtual steps and real steps. N may therefore be represented as:

$$N = \frac{2\theta_2 - 2\theta_1 + \beta}{\Delta\alpha} + 1 \qquad (6)$$

The total data collection is divided into three segments. The first segment is between virtual steps 1 to $n_1$ during which the detector does not move physically, but collects X-ray counts. During this segment, only the X-ray energy incident upon the region or pixels with the following x coordinates is projected to the cylindrical image.

$$x \le D\tan\left(n\cdot\Delta\alpha - \frac{\beta}{2}\right) \qquad (7)$$

or $$x \le D\tan\left(n\cdot\Delta\alpha - \arctan\frac{L}{2D}\right) \qquad (8)$$

The second segment is between step $n_1$ and $n_2$ during which the detector moves from the position S to the position E with the given scanning steps. During this segment, the X-ray energy incident upon all regions or pixels collected by the flat 2D detector is projected and stored into the cylindrical image. The total number of steps in this segment is $n_2-n_1$.

The third segment is between the virtual steps between $n_2$ and N. When the detector reaches the position E, it does not move further physically, but continues to collect the X-ray counts until the cylindrical image reaches homogenous exposure time up to the end point $2\theta_2$. In this segment, only the X-ray energy incident upon the region or pixels with the following x coordinates are projected and stored to the cylindrical image.

$$x \geq D \tan\left[(n - n_2) \cdot \Delta\alpha - \frac{\beta}{2}\right] \quad (9)$$

or $$x \geq D \tan\left[(n - n_2) \cdot \Delta\alpha - \arctan\frac{L}{2D}\right] \quad (10)$$

The above procedure assumes that no under travel and over travel space is available. In practice, however, there may be some space available beyond the desired 2θ range. Based on the same principles and methodology described above, one skilled in the art would be able to generate corresponding methods to make use the available extra space. Such methods might include, but would not be limited to, the following cases:

Space is available for under travel, but not available for over travel;
Space is not available for under travel, but available for over travel;
Space is partially available for under travel, but not for over travel;
Space is not available for under travel, but partially available for over travel;
Space is partially available for both under travel and over travel.

In each of these cases (and others), by following the procedure and methodology based on the concept of a virtual scan, a 2D diffraction pattern can be collected for the entire 2θ range between the two extreme positions of the detector.

Figure 12:
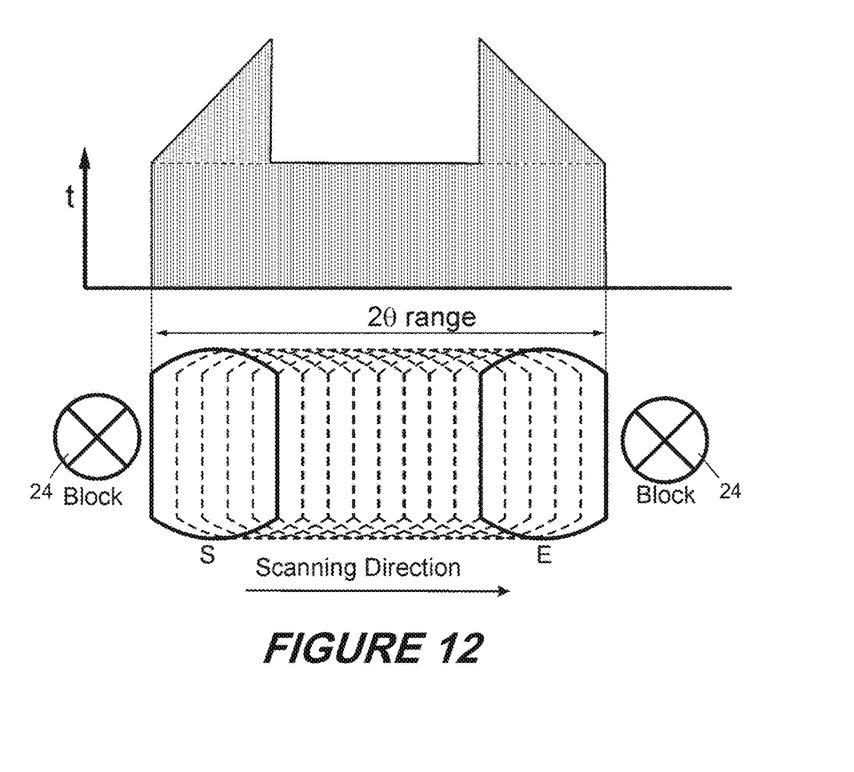
FIG. 12 is a schematic illustration of an alternative embodiment of the invention which uses extended exposure time at the extremes of the scanning range.

In an alternative embodiment of the invention, a diffraction pattern is collected without under travel or over travel by normalizing the diffraction intensity by the exposure time. FIG. 12 provides a schematic representation of this process, and shows the 2θ range of the detector with blocks 24 obstructing any additional travel. In this embodiment, rather than controlling which pixels are active in the physical detector, as in the embodiment above that uses the concept of a virtual detector, the X-ray energy collected by all of the pixels of the physical detector is used for all positions of the scan, but the detector remains stationary at the extreme positions for an extending period of data collection. This results in higher exposure time for some regions, but ensures a requisite minimum scan time at the extremes of the scanning range.

As shown in FIG. 12, the physical detector starts at position S and, rather than beginning the scanning movement right away, it stays at position S for a period equal to the time necessary to scan the angular range of the detector. For example, using the parameters shown in FIG. 11, if the data collection during the normal scanning mode has a scan time of $\Delta t$ for each scanning position, the total exposure time $T_S$ at position S will be $T_S = \Delta t(\beta/\Delta\alpha)$. After this period, the normal scan begins with the detector moving across the scan range with data collection for an exposure time of $\Delta t$ at each subsequent position until reaching the opposite extreme. At the position E, the physical movement of the detector stops, but there is an extended exposure time of $T_S$, as occurred at the position S.

This method ensures that there is a minimum exposure time for each of the scanning positions, but it also creates some scan regions that are exposed for a longer period than others. This can be seen in the top portion of FIG. 12, which shows that there are longer overall exposure times for certain scan regions due to the extended data collection at the extreme positions of the scan range. In order to get a final 2D image with an intensity based on homogeneous exposure time, the final pixel counts can be normalized by the exposure time. However, the normalization can only change the intensity (pixel counts), and not the counting statistics. Thus, for X-ray diffraction applications in which such inhomogeneous counting statistics would produce misleading results, the method described above using a virtual scan concept will produce more reliable diffraction data.

The invention claimed is:

1. A method for performing an X-ray diffraction measurement with an X-ray diffractometer that has an X-ray beam directed at a sample, that detects X-ray energy diffracted by the sample with a two-dimensional X-ray detector and that stores a representation of the detected X-ray energy as a spatial intensity distribution relative to a detection area comprising a cylindrical segment, the method comprising:
   moving the detector in an angular direction along a scanning path about a location of the sample while detecting the diffracted X-ray energy; and
   when the detector is located at an extreme of the scanning path, maintaining the position of the detector while detecting the X-ray energy, and progressively changing, along said angular direction, a portion of the X-ray energy being detected that is used to contribute to said representation of the detected X-ray energy.

2. A method according to claim 1 wherein the extreme of the scanning path is the beginning of the scanning path, and wherein progressively changing a portion of the X-ray energy being detected that is used to contribute to said representation comprises progressively increasing said portion before moving the detector along the scanning path.

3. A method according to claim 1 wherein the extreme of the scanning path is the end of the scanning path, and wherein progressively changing a portion of the X-ray energy being detected that is used to contribute to said representation comprises progressively decreasing said portion after moving the detector along the scanning path.

4. A method according to claim 1 wherein the detector is moved such that an angular range of said detection area for which detected X-ray energy is used to contribute to said representation changes at a predetermined speed, and wherein progressively changing a portion of the X-ray energy being detected that is used to contribute to said representation comprises changing said portion at a rate that matches said predetermined speed.

5. A method according to claim 1 wherein a spatial distribution of X-ray energy detected by the detector is transformed with a cylindrical projection prior to being used to contribute to said representation of the detected X-ray energy.

6. A method according to claim 5 wherein progressively changing a portion of the X-ray energy being detected that is used to contribute to said representation comprises progressively changing said portion along said angular direction after the detected X-ray energy is transformed with said cylindrical projection.

7. A method according to claim 1 wherein the detector moves along the scanning path with a stepwise motion.

8. A method according to claim 1 wherein the detector moves along the scanning path with a continuous motion.

9. A method according to claim 1 wherein the detector comprises a two-dimensional array of pixels.

10. A method according to claim 9 wherein changing a portion of the X-ray energy being detected that is used to contribute to said representation comprises changing the pixels from which detected X-ray energy is used for contributing to said representation.

11. A method according to claim 10 wherein pixel columns in the detector are perpendicular to the scanning path, and wherein changing the pixels from which detected X-ray energy is used comprises changing the pixels column-by-column in a direction perpendicular to the pixel columns.

12. A method according to claim 9 wherein a spatial distribution of X-ray intensities detected by the pixels in the plane of the detector is stored as a spatial distribution of X-ray intensities in a cylindrical projection of the detector pixels that substantially corresponds to the detection area.

13. A method according to claim 12 wherein changing the portion of the X-ray energy being detected that is used to contribute to said representation comprises changing the pixels, as projected in the cylindrical projection, from which said X-ray intensities are used column-by-column along a direction of the scanning path.

14. An X-ray diffractometer for performing an X-ray diffraction measurement of a sample comprising:
an X-ray beam directed at the sample;
a two-dimensional X-ray detector that detects X-ray energy diffracted by the sample; and
a scanning system that moves the detector in an angular direction along a scanning path about a location of the sample while detecting the diffracted X-ray energy and stores a representation of the detected X-ray energy as a spatial intensity distribution relative to a detection area comprising a cylindrical segment wherein, when the detector is located at an extreme of the scanning path, the position of the detector is maintained while detecting the X-ray energy, and a portion of the X-ray energy being detected that is used to contribute to said representation of the detected X-ray energy is progressively changed along said angular direction.

15. A diffractometer according to claim 14 wherein the extreme of the scanning path is the beginning of the scanning path, and wherein the portion of the X-ray energy being detected that is used to contribute to said representation is progressively increased before moving the detector along the scanning path.

16. A diffractometer according to claim 14 wherein the extreme of the scanning path is the end of the scanning path, and wherein the portion of the X-ray energy being detected that is used to contribute to said representation is progressively decreased after moving the detector along the scanning path.

17. A diffractometer according to claim 14 wherein the detector is moved such that an angular range of said detection area for which detected X-ray energy is used to contribute to said representation changes at a predetermined speed, and wherein progressively changing a portion of the X-ray energy being detected that is used to contribute to said representation comprises changing said portion at a rate that matches said predetermined speed.

18. A diffractometer according to claim 14 wherein the scanning system transforms a spatial distribution of X-ray energy detected by the detector with a cylindrical projection prior to it being used to contribute to said representation of the detected X-ray energy.

19. A diffractometer according to claim 18 wherein the portion of the X-ray energy being detected that is used to contribute to said representation of the detected X-ray energy is progressively changed along said angular direction after the detected X-ray energy is transformed with said cylindrical projection.

20. A diffractometer according to claim 14 wherein the scanning system moves the detector along the scanning path with a stepwise motion.

21. A diffractometer according to claim 14 wherein the scanning system moves the detector along the scanning path with a continuous motion.

22. A diffractometer according to claim 14 wherein the detector comprises a two-dimensional array of pixels.

23. A diffractometer according to claim 22 wherein the portion of the X-ray energy being detected that is used to contribute to said representation is changed by changing the pixels from which detected X-ray energy is used for contributing to said representation.

24. A diffractometer according to claim 23 wherein pixel columns in the detector are perpendicular to the scanning path, and wherein the pixels from which detected X-ray energy is used are changed column-by-column in a direction perpendicular to the pixel columns.

25. A diffractometer according to claim 22 wherein a spatial distribution of X-ray intensities detected by the pixels in the plane of the detector is stored as a spatial distribution of X-ray intensities in a cylindrical projection of the detector pixels that substantially corresponds to the detection area.

26. A diffractometer according to claim 25 wherein changing the portion of the X-ray energy being detected that is used to contribute to said representation comprises changing the pixels, as projected in the cylindrical projection, from which said X-ray intensities are used column-by-column along a direction of the scanning path.

27. A method for performing an X-ray diffraction measurement with an X-ray diffractometer having an X-ray beam directed at a sample and a two-dimensional X-ray detector that collects X-ray energy diffracted by the sample, the method comprising:
performing a scan by collecting said diffracted X-ray energy while moving the detector through a scanning range in an angular direction about a location of the sample at a speed of $\Delta\alpha/\Delta t$, where $\Delta\alpha$ is an angular distance that corresponds to the distance between adjacent columns of detector pixels perpendicular to the scan direction;
when the detector is located at an extreme of the scanning range, maintaining the position of the detector and actively collecting said diffracted X-ray energy for a duration of $N(\Delta t)$, where N is the number of said pixel columns; and
normalizing a measured intensity of the diffracted X-ray energy collected by the detector relative to exposure time.

28. A method according to claim 27 wherein said extreme of the scanning range is the beginning of the scanning range.

29. A method according to claim 27 wherein said extreme of the scanning range is the end of the scanning range.

30. A method according to claim 27 wherein, when the detector is moving, an exposure time for the detector is substantially the same for any angular position along the scanning range.

31. A method according to claim 27 wherein the detector moves through the scanning range with a stepwise motion.

32. A method according to claim 27 wherein the detector moves through the scanning range with a continuous motion.

* * * * *